United States Patent

Gonella

Patent Number: 5,665,377
Date of Patent: Sep. 9, 1997

[54] ADMINISTRATION SYSTEM FOR ESTRADIOL

[75] Inventor: Jacques Gonella, Muttenz, Switzerland

[73] Assignee: Giapharma SA, Zug, Switzerland

[21] Appl. No.: 358,897

[22] Filed: Dec. 19, 1994

Related U.S. Application Data

[63] Continuation of Ser. No. 58,517, May 3, 1993, abandoned.

[51] Int. Cl.[6] .................................................. A61F 13/02
[52] U.S. Cl. .................................... 424/448; 424/449
[58] Field of Search ................................. 424/448, 449

[56] References Cited

U.S. PATENT DOCUMENTS

| | | | |
|---|---|---|---|
| 4,390,520 | 6/1983 | Nagai et al. | 424/28 |
| 4,816,258 | 3/1989 | Nedberge et al. | 424/448 |
| 4,818,540 | 4/1989 | Chien et al. | 424/448 |
| 5,023,084 | 6/1991 | Chien et al. | 424/448 |
| 5,122,382 | 6/1992 | Gale et al. | 424/449 |
| 5,145,682 | 9/1992 | Chien et al. | 424/448 |
| 5,393,529 | 2/1995 | Hoffmann et al. | 424/445 |

*Primary Examiner*—Jyothsan Venkat
*Attorney, Agent, or Firm*—Seed and Berry LLP

[57] ABSTRACT

The adhesive plaster for the transdermal administration of estradiol or mixture estradiol/progestin is composed of an impermeable carrier film and of an adhesive composition. The latter represents a matrix or reservoir layer and is composed of a solvent-based polyacrylate or polyisobutylene adhesive which contains a saturated or unsaturated fatty acid with 6 to 18 C atoms as permeability enhancer, estradiol or mixture estradiol/progestin as active substance and optionally propylene glycol as solvent.

The adhesive plaster is used for the systemic administration of hormones in hormone replacement therapy for a time of at least 3 days.

8 Claims, No Drawings

ADMINISTRATION SYSTEM FOR ESTRADIOL

This application is a continuation of application Ser. No. 08/058,517 filed May 3, 1993, now abandoned.

The present invention relates to a percutaneous (or transdermal) administration system for estradiol, alone or in combination with a progestin. This administration system is an adhesive plaster which contains an adhesive composition which contains the active substance and which is applied to an impermeable carrier film. Sticking on the adhesive plaster results in a virtually constant rate of release of the hormone for a period of at least 3 days. The system additionally contains a permeability enhancer which reduces the resistance of the skin to diffusion of the active substance.

Estradiol is the main estrogen secreted by the female gonad during the fertile years of life. At an age of 45 to 50 years the menses cease owing to a decrease in ovarian function, and women enter the so-called climacterium.

The deficiency of hormone secretion leads in many women to development of vasomotor signs and symptoms (hot flushes, sweating) as well as sleep distrubances, anxiety states and atrophy of hormone-controlled organs, such as in the mammary glands and the vaginal epithelium. These symptoms and signs are called the menopausal syndrome. In addition to this, the low level of hormone secretion likewise leads to an increase in cardiovascular disorders and the development of osteoporosis.

Hormone replacement therapy (HRT) alleviates not only the menopausal syndrome but also any rarefaction of bone which is present, and reduces the cardiovascular risk. It has been found advantageous to administer also an amount of progestin as a part of such steroid replacement therapy. Prefered progestins are norethindrone, α-Ketodesogestrel, desogestrel, demegestone, chlormadinone acetate or nomegestrol.

Although oral administration of estrogens has proven effective, percutaneous administration of HRT has potential advantages over the oral route because it avoids preceding metabolism (first pass effect) in the liver and in the jejunal mucosa.

Various devices for the percutaneous administration of estrogen have been proposed. U.S. Pat. No. 4,379,454 discloses a reservoir which contains estradiol dissolved in ethanol; a penetration-controlling membrane separates the reservoir from the skin. However, this type of device has various disadvantages. The adhesive to attach the system to the skin must be present (as a ring) outside the core which contains the hormone, which results in a limited adhesive area being available and unnecessarily increases the total area of the system. In addition, ethanol has a tendency to reduce the strength of the adhesive and to bring about a loss of adhesiveness. If, in addition, the system detaches and falls off the skin, and the patient attempts to attach it at a new site, the hormone penetration is diminished because most of the carrier or sorption promoter (ethanol) is used up.

The devices proposed in the prior art have in common the addition of permeability adjuvants to the active principle in order to achieve the required level of reproduction and the necessary degree of permeability: these adjuvants are called permeability improvers or enhancers or else carriers. Acetone, dimethyl sulfoxide (DMSO), ethanol, propylene glycol and unsaturated long-chain fatty acids are the most usual substances which are known for increasing the degree of permeability of various active substances and hormones (R. W. Baker and J. Farrand "Patents in transdermal drug delivery" Drug Delivery Systems 1987, Conference Proceedings). DMSO has not been approved by the FDA for medicinal use in humans.

U.S. Pat. No. 4,390,520 discloses the use of a transdermal release system in which the active principle is dispersed or dissolved in an adhesive. The active substance then diffuses from the adhesive through the skin. One of the problems associated with the use of transdermal devices comprises the difficulty of achieving an appropriate level of effect and a predetermined dosage during a preset time for a pharmaceutical composition. Furthermore, it must be possible to produce the system economically on the industrial scale, and the system must be stable for a relatively long time (18 to 24 months) in order to allow commercial utilization thereof.

The aim of the present invention comprises the provision of a uniform transdermal device which makes possible an appropriate hormone permeability in order to achieve, in post-menopausal women, a plasma hormone level which corresponds to that necessary for hormone replacement therapy. Another aim comprised the finding of an appropriate hormone permeability enhancer which brings about a high hormone flux and thus allows therapeutic adhesive plasters to be produced in a small size. The main aim of the present invention comprised the finding of fatty acids or of a mixture of polyols and fatty acids which simultaneously permits an appropriate increase in the hormone permeability and, at the same time, can easily be produced industrially.

The present invention accordingly relates to the adhesive plaster defined in claim 1 for the transdermal administration of estradiol (or combination estradiol/progestin) and to the process defined in claim 5 for the production thereof.

The adhesive composition employed according to the invention accordingly comprises an appropriate mixture of estradiol (or combination estradiol/progestin) with a medicinally acceptable adhesive, preferably selected from the polyisobutylenes or acrylic adhesives in combination with polyethylene glycol and/or lauric acid. The hormone content of the adhesive is in the range 0.5–3% by weight. The amount of hormone should be kept at a minimum in order to maintain pseudozero order permeability for a time of at least 3 days,. If this concentration is exceeded, there is an increased possibility of hormone precipitating out and likewise of crystals being formed during the storage of the medicinal product. As suggested above, it is necessary to add a permeability enhancer to the system in order to obtain a preset plasma level of hormone which is independent of individual differences in the structure of the skin. Long-chain fatty acids with one or more double bonds, such as oleic acid, have frequently been used for this purpose together with alkylenediols such as propylene glycols. This type of binary system has been proposed in EP-A 0 171742 for a transdermal administration of the non-steroidal active substance naloxone. There is no disclosure in this document that combination of a saturated or unsaturated fatty acid with polyethylene glycol is effective for the production of an improved transdermal release system for releasing a therapeutically effective dose of a steroid, especially of estradiol.

Tests which have been carried out have shown that lauric acid confers high permeability properties on the transdermal device without impairing the pharmaceutical stability of the hormone in the system, and likewise the mixture does not induce hormone crystallization.

The present invention is explained in detail by the following examples without a limitation being intended thereby.

EXAMPLES

All the starting materials needed to produce the transdermal adhesive plasters according to the present invention are known. All the concentrations are indicated in percentages by weight unless otherwise indicated.

The adhesive polymer is an adhesive which is approved for medicinal use. Of these polymer types, those based on solvent are preferred. This polymer type has two purposes in the present invention: Firstly: it brings about the adhesion to the skin and the secure retention of the transdermal device facilitates transfer of estradiol and lauric acid onto and into the skin by bringing about good diffusion contact. Secondly: it acts as matrix or reservoir layer for storage of the hormone, its solvent propylene glycol and/or a C6–C18-fatty acid such as lauric acid. The adhesive polymer is preferably a vinyl acetate/acrylate multipolymer. Multipolymers of this type are obtainable from MONSANTO Co., St. Louis, Mo. under the tradename GELVA.

The production of an adhesive plaster for transdermal administration is carried out as follows. Estradiol (or mixture estradiol/progestin), preferably in the microcrystalline pharmaceutical form, is dissolved in the solvent together with the permeability enhancer in order to form a solution (solution A). Simultaneously, the acrylic polymer is brought to the working consistency by, if necessary, adding ethyl acetate (solution B). Subsequently, the two solutions are mixed cautiously, avoiding bubble formation, but thoroughly for 60 minutes. In the next stage, the solvents which are introduced into the system by solution B are evaporated off under vacuum and at a temperature between 25°–30° C. until the solids content is 30%.

The mixture is then poured onto the carrier membrane (preferably composed of polyethylene film, such as, for example, products of the 3M company) to a thickness of 0.2 mm. The poured material is dried in a drying tunnel at an appropriate temperature in order to evaporate off the residual solvent during the stay in the tunnel. After the drying, the film is laminated with a protective or covering film such as silicone-coated polyester or the like. The produced adhesive plasters are then cut to an appropriate shape. They should be stored in closed containers in order to protect them from moisture and air.

Example 1

Transdermal adhesive plasters are produced as described above. The estradiol content is 2%, lauric acid 10% and propylene glycol 20%. Table 1 shows the "in vitro" degree of permeability through nude mouse skin using a one-compartment diffusion cell at a temperature of 32° C.

TABLE 1

| Time (h) | Flux μg/cm²/h |
| --- | --- |
| 0 | 0 |
| 3 | 0.6 |
| 6 | 1.2 |
| 12 | 1.4 |
| 24 | 1.2 |

Example 2

A similar administration system as that according to Example 1 was tested on heat-insulated stratum corneum from human skin.

TABLE 2

| Time (h) | Flux μg/cm²/h |
| --- | --- |
| 0 | 0 |
| 3 | 0.24 |

TABLE 2-continued

| Time (h) | Flux μg/cm²/h |
| --- | --- |
| 6 | 0.36 |
| 12 | 0.88 |
| 24 | 0.92 |

Example 3

Similar administration systems as those according to Examples 1 and 2 were punched out to a size of 15 cm² and applied to the forearms of postmenopausal women who had volunteered to take part in the study. A total of 6 women retained the device for 3 days. Blood samples were taken after predetermined times, and the estradiol content of the plasma was measured by standard radioimmunoassays. The values are presented in Table 3. It should be noted that the adhesive plasters were removed after the 72-hour sampling.

TABLE 3

| Time (h) | Plasma estradiol pg/ml |
| --- | --- |
| 0 (basal) | 12 ± 8 |
| 12 | 48 ± 6 |
| 24 | 66 ± 9 |
| 48 | 58 ± 12 |
| 72 | 52 ± 11 |
| 96 | 14 ± 10 |

Example 4

Transdermal adhesive plasters are produced as described above. The estradiol content is 2,44% and lauric acid is 12%. The results of permeability are equivalent to the results obtained with adhesive plasters described in example 1.

I claim:

1. An adhesive plaster for the transdermal administration of estradiol, which is composed of an impermeable carrier film and of an adhesive composition coated thereon, wherein the adhesive composition, which represents a matrix or reservoir layer, is a solvent-based polyacrylate or polyisobutylene adhesive which contains lauric acid as permeability enhancer at a concentration of 1 to 25% and estradiol as an active substance at a concentration of 0.5 to 3%.

2. The adhesive plaster according to claim 1, wherein the adhesive composition comprises propylene glycol as solvent.

3. The adhesive plaster according to claim 1, wherein the matrix contains 0.5 to 3.0% estradiol,
1 to 25% lauric acid, and
0 to 30% propylene glycol.

4. A process for producing an adhesive plaster according to claim 1, which comprises:

(a) producing a solution A which contains 0.5 to 3% estradiol, 1 to 25% lauric acid and optionally propylene glycol as a pharmaceutically acceptable solvent, and a solution B which contains polyacrylate and a pharmaceutically acceptable solvent;

(b) mixing the resulting solutions A and B;

(c) partly evaporating off the solvent; and (d) applying the mixture to an impermeable carrier film.

5. The adhesive plaster according to claim 1, wherein the lauric acid is at a concentration of 1 to 15%.

6. The adhesive plaster according to claim 1, wherein the lauric acid is at a concentration of 1 to 12%.

7. The adhesive plaster according to claim 1, wherein the estradiol is at a concentration of 1 to 3%.

8. The adhesive plaster according to claim 1, wherein the estradiol is at a concentration of 1.5 to 2.5%.

* * * * *